US010426942B2

(12) United States Patent
Kang (10) Patent No.: US 10,426,942 B2
(45) Date of Patent: Oct. 1, 2019

(54) CONNECTION STRUCTURE FOR IV TUBE OF IV INFUSION SET

(71) Applicant: MEDILINE ACTIVE KOREA CO., LTD., Ansan-si (KR)

(72) Inventor: Dae Won Kang, Seoul (KR)

(73) Assignee: MEDILINE ACTIVE KOREA CO., LTD., Ansan-si (KR)

(*) Notice: Subject to any disclaimer, the term of this patent is extended or adjusted under 35 U.S.C. 154(b) by 0 days.

(21) Appl. No.: 15/539,498

(22) PCT Filed: Nov. 3, 2016

(86) PCT No.: PCT/KR2016/012558
§ 371 (c)(1),
(2) Date: Jun. 23, 2017

(87) PCT Pub. No.: WO2017/171179
PCT Pub. Date: Oct. 5, 2017

(65) Prior Publication Data
US 2018/0050185 A1 Feb. 22, 2018

(30) Foreign Application Priority Data
Mar. 31, 2016 (KR) .................. 10-2016-0039269

(51) Int. Cl.
*A61M 39/10* (2006.01)
*A61M 5/14* (2006.01)
(Continued)

(52) U.S. Cl.
CPC ....... *A61M 39/1011* (2013.01); *A61M 5/1411* (2013.01); *A61M 5/158* (2013.01);
(Continued)

(58) Field of Classification Search
CPC .. A61M 39/1011; A61M 39/10; A61M 39/22; A61M 5/1411; A61M 5/158;
(Continued)

(56) References Cited

U.S. PATENT DOCUMENTS 4,668,217 A * 5/1987 Isono .................... A61M 39/10
604/29
7,901,386 B2 * 3/2011 Hishikawa ............. A61M 5/14
604/258
(Continued)

FOREIGN PATENT DOCUMENTS

DE 3314640 A1 11/1983
JP 2004173844 A 6/2004
(Continued)

OTHER PUBLICATIONS

The extended European search report of EP 16 87 4100, dated Jun. 18, 2018.

*Primary Examiner* — Bhisma Mehta
*Assistant Examiner* — Hazma A Darb
(74) *Attorney, Agent, or Firm* — STIP Law Group, LLC (57) ABSTRACT

Disclosed is a connection structure for an IV tube of an IV infusion set, in which an IV tube is firmly connected by fitting using a connector without using an adhesive, thereby preventing bacterial infection. The connection structure is configured such that an outlet provided in an IV bag is connected to a drip chamber, the IV tube is connected to the drip chamber to allow an IV fluid to flow, an end of the IV tube is connected to an injection site for injecting the IV fluid, wherein a connector is provided on an outer circumferential surface of the IV tube that is connected to the drip chamber and the injection site, thereby locking the IV tube.

12 Claims, 6 Drawing Sheets

(51) Int. Cl.
*A61M 5/158* (2006.01)
*A61M 39/22* (2006.01)
*A61J 1/10* (2006.01)

(52) U.S. Cl.
CPC ............ *A61M 39/22* (2013.01); *A61J 1/10* (2013.01); *A61M 2039/229* (2013.01); *A61M 2205/75* (2013.01)

(58) Field of Classification Search
CPC ........ A61M 2039/229; A61M 2205/75; A61M 2039/2433; A61M 2039/2446; A61J 1/10
See application file for complete search history.

(56) References Cited

U.S. PATENT DOCUMENTS

| 2005/0104374 | A1* | 5/2005 | Steur | F16L 33/223 285/247 |
|---|---|---|---|---|
| 2008/0058720 | A1* | 3/2008 | Spohn | A61M 5/007 604/140 |
| 2008/0287867 | A1* | 11/2008 | Yow | A61M 5/162 604/86 |
| 2011/0270230 | A1* | 11/2011 | Sage | A61M 39/1011 604/533 |
| 2015/0308598 | A1 | 10/2015 | Lewis et al. | |
| 2015/0327927 | A1* | 11/2015 | Larson | A61B 18/02 165/11.1 |

FOREIGN PATENT DOCUMENTS

| JP | 2004321788 A | 11/2004 |
|---|---|---|
| KR | 2020130002532 A | 4/2013 |
| KR | 1020140024760 A | 3/2014 |
| KR | 1020140065198 A | 5/2014 |
| KR | 101553228 B1 | 9/2015 |

* cited by examiner

CONNECTION STRUCTURE FOR IV TUBE OF IV INFUSION SET

CROSS-REFERENCE TO RELATED APPLICATIONS

This application is the U.S. National Phase under 35 U.S.C. § 371 of International Application No. PCT/KR2016/012558 filed on Nov. 3, 2016, which in turn claims the benefit of Korean Application No. 10-2016-0039269, filed on Mar. 31, 2016, the disclosures of which are incorporated by reference into the present application.

TECHNICAL FIELD

The present invention relates generally to a connection structure for an IV tube of an IV infusion set. More particularly, the present invention relates to a connection structure for an IV tube of an IV infusion set, in which the IV tube is firmly connected by fitting using a connector without using an adhesive, thereby preventing bacterial infection.

BACKGROUND ART

Generally, IV fluids such as physiological saline and glucose used in hospitals that treat patients or perform surgery are stored in IV fluid containers of a certain shape, and IV fluid containers are largely differentiated into IV bottles and IV bags depending on the material of the container.

Since conventional IV bottles are easily broken and require special care when handling, IV bags made of flexible materials have recently become widely used. Such containers are less likely to be damaged than conventional IV bottles and are easy to use and dispose.

Further, in order to inject the IV fluid contained in the IV bag into a patient, an IV infusion set connected to the IV bag is provided to deliver the IV fluid to the patient's blood vessel.

Figure 1:
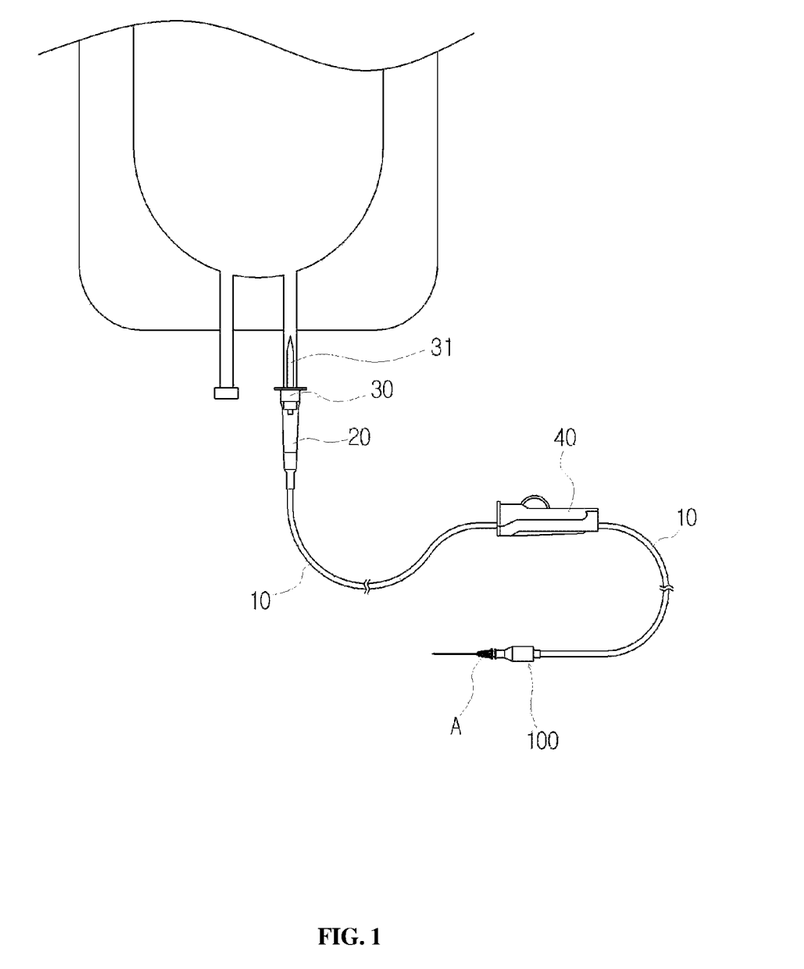
FIG. 1 shows a front view of a configuration of a conventional IV infusion set.

As shown in FIG. 1, a conventional IV infusion set includes: a combined body 30 for drawing an IV fluid contained in an IV bag by inserting a spike 31 into a rubber packing in a sealing cap coupled to an outlet of the IV bag; a drip chamber 20 connected to the combined body 30 to temporarily store the IV fluid drawn from the spike 31; an IV tube 10 communicatively connected to a second end of the drip chamber 20 to allow the IV fluid to flow; a connection portion 100 connected to a second end of the IV tube 10 such that a needle A for injecting the IV fluid into a patient's blood vessel is connected to the tube; and a roller clamp 40 coupled to an outside of the IV tube 10 to press the soft IV tube 10, such that the amount of the IV fluid dripping from the IV bag is regulated by controlling a communication area of the IV fluid in the IV tube 10.

Meanwhile, the conventional IV infusion set is configured such that the IV tube 10, in which the IV fluid flows, is inserted into the drip chamber 20 and the connection part 100, and then locked thereto by using an adhesive.

As described above, since the IV tube of the conventional IV infusion set is locked by using an adhesive, the adhesive penetrates into the IV tube and is injected into the patient along with the IV fluid, thereby causing problems such as bacterial infection

DOCUMENTS OF RELATED ART

Patent Document (Patent Document 1) Korean Utility Model Application Publication No. 20-2013-0002532

DISCLOSURE

Technical Problem

Accordingly, the present invention has been made keeping in mind the above problems occurring in the prior art, and an object of the present invention is to provide a connection structure for an IV tube of an IV infusion set, in which an IV tube, through which an IV fluid flows, is connected to each connection portion of an IV infusion set by using a connector, so the IV tube is locked by fitting of the connector without using an adhesive, which is conventionally used, whereby it can be safely used without harming the human body, and the IV tube can be easily connected by using the connector, thereby improving the work convenience.

Technical Solution

In order to accomplish the above object, according to some aspect of the present invention, there is provided a connection structure for an IV tube of an IV infusion set, in which an outlet provided on an IV bag is connected to a drip chamber, an IV tube is connected to the drip chamber to allow an IV fluid to flow, an injection site for injecting the IV fluid into a patient is connected to an end of the IV tube, and a Y-port, a three-way stopcock, a filter, a luer lock, in addition to the drip chamber and the injection site are connected to the IV tube, includes a connector provided on an outer circumferential surface of the IV tube to lock the IV tube, with at least one of the drip chamber, the injection site, the Y-port, the three-way stopcock, the filter, and the luer lock being connected to the IV tube.

The connector may be formed in an annular ring shape to be fitted over the outer circumferential surface of the IV tube, with an insertion part being provided in the connector to allow the IV tube to be inserted therein.

The insertion part may be tapered downward such that the IV tube is firmly connected to the drip chamber and the injection site.

The insertion part may be provided on an inner wall thereof with a compression piece to press the IV tube against the drip chamber and the injection site when the IV tube is connected to the drip chamber and the injection site such that the IV tube is prevented from being separated therefrom.

The compression piece may protrude outwardly from the inner wall of the insertion part to be in any one of a triangular, a rectangular, and a round shape.

The compression piece may be provided in a band shape or a dot shape around the inner wall of the insertion part.

The IV tube may be connected with the drip chamber, the injection site, the Y-port, the three-way stopcock, the filter, and the luer lock, wherein the IV tube is connected with each of the drip chamber, the injection site, the Y-port, the three-way stopcock, the filter, and the luer lock, by using the connector.

Advantageous Effects

A connection structure for an IV tube of an IV infusion set according to the present invention is advantageous in that since an IV tube, which supplies an IV fluid by being connected to a drip chamber and an injection site, is firmly locked to the drip chamber and the injection site by using a connector without using an adhesive, as is conventionally used, it is harmless to the human body, thereby increasing patient trust.

The present invention is further advantageous in that since the connector is connected to the IV tube by fitting, the work convenience and the work efficiency are maximized.

BEST MODE

Herein below, exemplary embodiments of the present invention will be described in detail with reference to the accompanying drawings.

Figure 2:
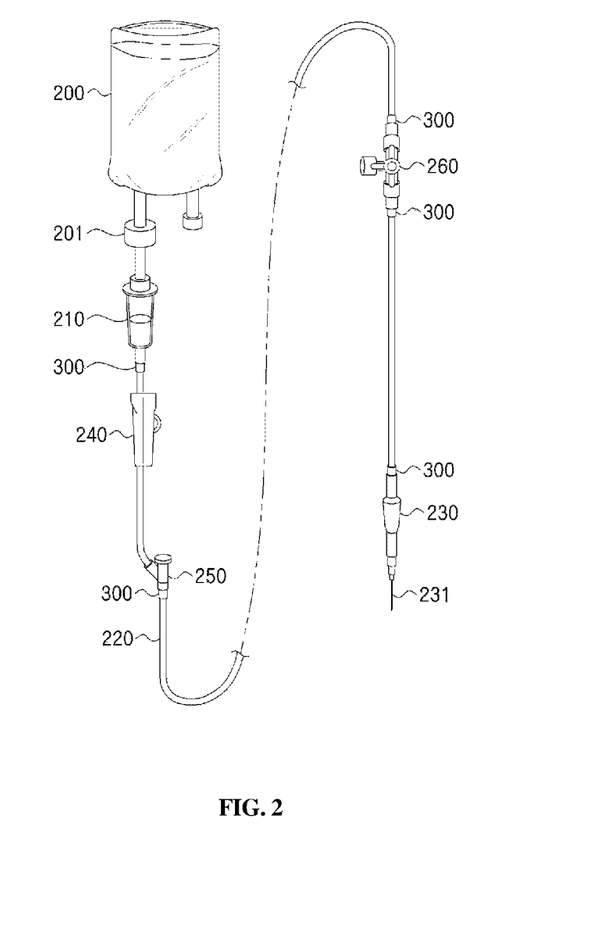
FIG. 2 shows a front view of a configuration of an IV infusion set according to the present invention.
Figure 3:
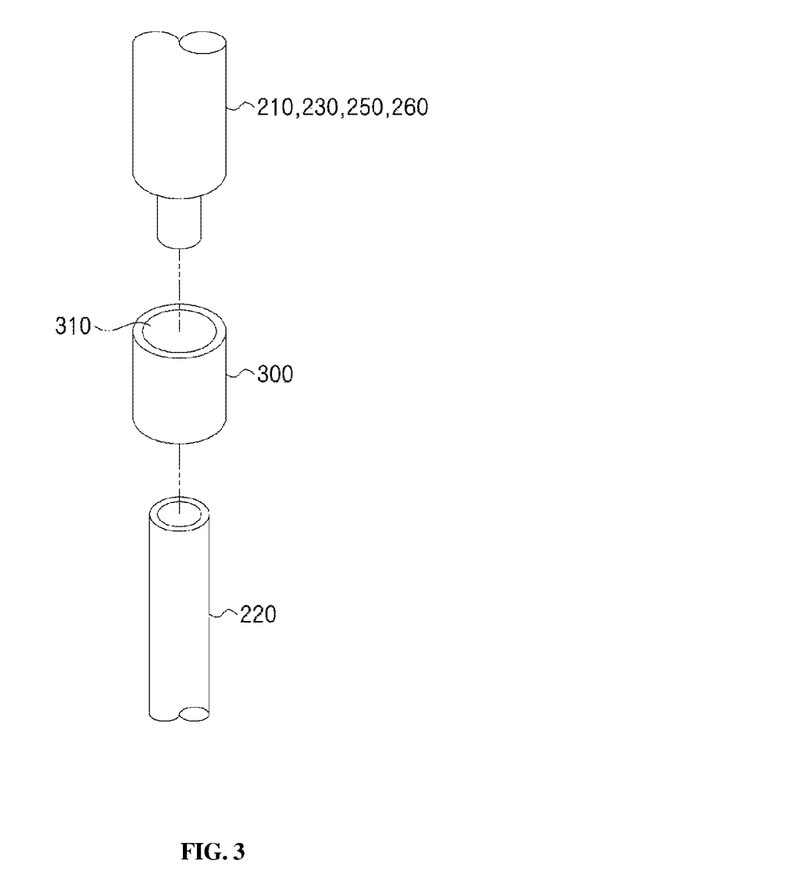
FIG. 3 shows an exploded perspective view of an IV tube of the IV infusion set according to the present invention.
Figure 4:
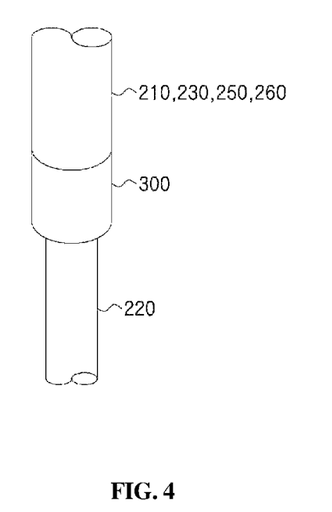
FIG. 4 shows an assembled perspective view of the IV tube of the IV infusion set according to the present invention.
Figure 5:
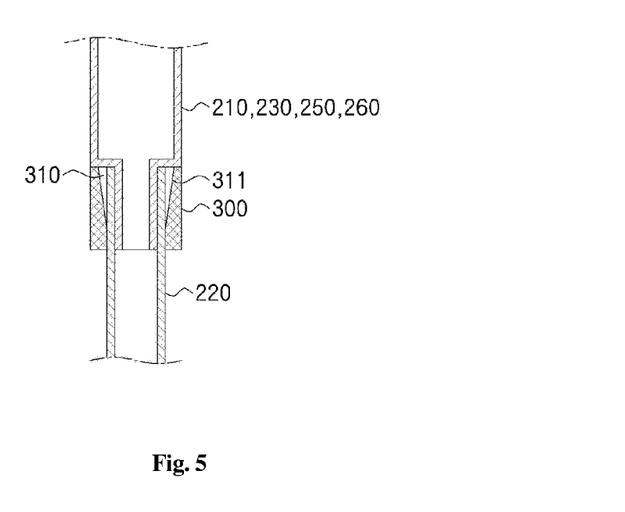
FIG. 5 shows an assembled sectional view of the IV tube of the IV infusion set according to the present invention.
Figure 6:
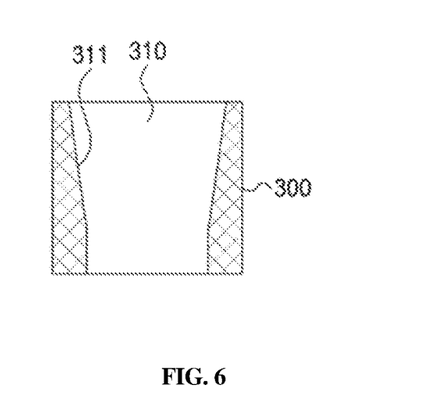
FIG. 6 shows a sectional view of a connector for connecting the IV tube of the IV infusion set according to the present invention.
Figure 7:
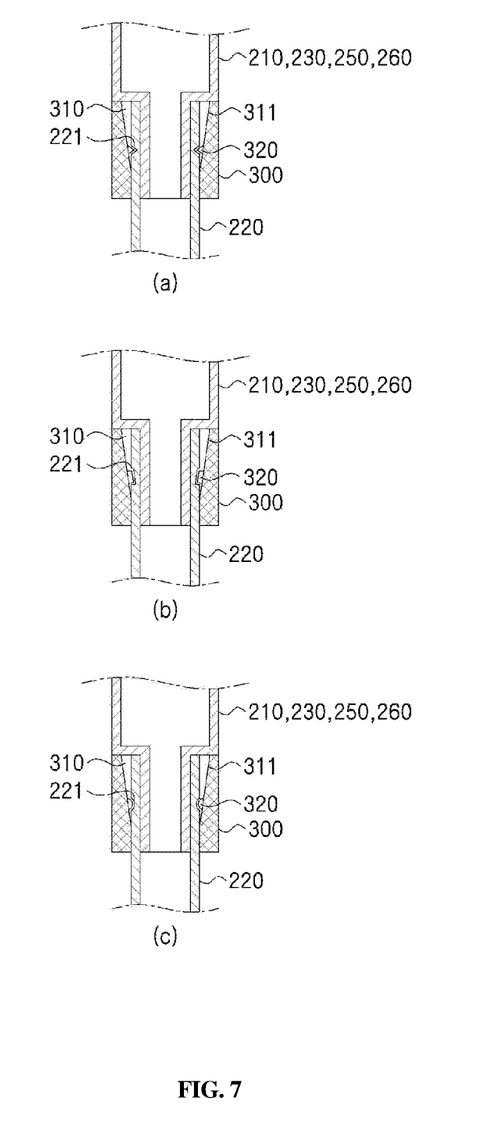
FIG. 7 shows sectional views of examples of the connector for connecting the IV tube of the IV infusion set according to the present invention.

FIG. 2 shows a front view of a configuration of an IV infusion set according to the present invention; FIG. 3 shows an exploded perspective view of an IV tube of the IV infusion set according to the present invention; FIG. 4 shows an assembled perspective view of the IV tube of the IV infusion set according to the present invention; FIG. 5 shows an assembled sectional view of the IV tube of the IV infusion set according to the present invention; FIG. 6 shows a sectional view of a connector for connecting the IV tube of the IV infusion set according to the present invention; and FIG. 7 shows sectional views of examples of the connector for connecting the IV tube of the IV infusion set according to the present invention.

As shown in FIGS. 2 to 6, an IV infusion set according to the present invention includes: an IV bag 200 in which an IV fluid is stored; a drip chamber 210 connected to an outlet 201 of the IV bag 200 to temporarily store the IV fluid dripping from the IV bag 200; an IV tube 220 connected to the drip chamber 210 to allow the IV fluid temporarily stored in the drip chamber 210 to flow; and an injection site 230 connected to a second end of the IV tube 220 to connect a needle 231 for injecting an IV fluid into a patient's blood vessel.

Further, the IV tube 220 connected to the drip chamber 210 and the injection site 230 is provided with all the components of the IV infusion set, such as a flow control clamp 240, a Y-port 250, a three-way stopcock 260, and the like.

In other words, the IV tube 220 for supplying the IV fluid is connected between the IV bag 200 and the injection site 230 to supply the IV fluid dripping from the IV bag 200 to the injection site 230, whereby it is possible to inject the IV fluid into the patient's blood vessel through the needle 231.

As shown in FIG. 2, a connection structure for the IV tube of the IV infusion set according to the present invention is configured such that the IV tube 220 is connected to the drip chamber 210 and the injection site 230 by using connectors 300.

In other words, the IV tube 220 for supplying the IV fluid dripping through the drip chamber 210 is fitted over outer circumferential surfaces of the drip chamber 210 and the injection site 230, and the connector 300 is pushed to an assembly portion of the IV tube 220 to firmly lock the IV tube 220.

The connector 300 is formed in an annular ring shape corresponding to a shape of the IV tube 220, so as to lock the IV tube 220 for supplying the IV fluid to the drip chamber 210, the injection site 230, and all the components of the IV infusion set, such as the Y-port 250, the three-way stopcock 260, and the like.

As described above, the connector is applied to each of the drip chamber 210, the injection site 230, the Y-port 250, the three-way stopcock 260, and all the components of the IV infusion set, such as an IV-filter, a mini-volume filter, a male lure lock, a female lure lock, a rotate lure lock, and the like, which are not shown in the drawings.

Further, an insertion part 310 is formed in the connector 300 to allow the IV tube 220 to be inserted therein.

Thereby, in the state where the IV tube 220 is inserted into the insertion part 310, and the IV tube 220 is connected to the drip chamber 210 and the injection site 230, the connectors 300 are pushed to press the connectors 300 against the IV tube 220, such that IV tube 220 is firmly locked to the drip chamber 210 and the injection site 230.

As shown in FIG. 6, the insertion part 310 is formed with a tapered portion 311, such that the IV tube 220 is firmly connected to the IV infusion set, that is, to the drip chamber 210, the injection site 230, the Y-port 250, and the three-way stopcock 260.

In other words, the tapered portion 311 allows the connector 300 to smoothly move along the IV tube 220 when the connectors 300 are put on the outer circumferential surface of the IV tube 220, and then are pushed toward the assembly portions of the drip chamber 210, the injection site 230, the Y-port 250, and the three-way stopcock 260 in the state where the IV tube 220 is connected the IV infusion set, that is, to the drip chamber 210, the injection site 230, the Y-port 250, and the three-way stopcock 260, thereby locking the IV tube 220.

Further, since the insertion part 310 is formed with the tapered portion 311, an end of the insertion part 310 maximally presses the IV tube 220 that is connected the IV infusion set, that is, to the drip chamber 210, the injection site 230, the Y-port 250, and the three-way stopcock 260, whereby the IV tube 220 is firmly locked to the IV infusion set without separating therefrom.

As shown in FIG. 7, an inner wall of the insertion part 310 is provided with a compression piece 320 to maximally press the IV tube 220 against the IV infusion set when the IV tube 220 is connected to the IV infusion set, that is, to the drip chamber 210, the injection site 230, the Y-port 250, and the three-way stopcock 260, whereby the IV tube 220 is prevented from being separated therefrom.

Further, the compression piece 320 is provided outwardly from the inner wall of the insertion part 310, and as shown in FIG. 7(a), it may be provided in a triangular shape, as shown in FIG. 7(b), in a rectangular shape, or as shown in FIG. 7(c), in a round shape.

As described above, since the insertion part 310 of the connector 300 is provided with the compression piece 320 formed in various shapes, it is possible to maximally press the IV tube 220 against the drip chamber 210, the injection site 230, the Y-port 250, and the three-way stopcock 260 when the connector 300 locks the IV tube 220, whereby it is possible to prevent separation of the IV tube 220, and to increase safety.

Meanwhile, the compression piece 320 may be provided in a band shape or a dot shape around the inner wall of the insertion part 310.

Further, as shown in FIG. 7, the outer circumferential surface of the IV tube 220 is formed with an anti-separation groove 221 at a location corresponding to the compression piece 320, such that the compression piece 320 is engaged therewith, thereby preventing the IV tube 220 from being separated.

Here, it is preferred that the anti-separation groove 221 is formed in the same shape as the shape of the compression piece 320.

The operation of the connection structure for the IV tube of the IV infusion set of the present invention configured as described above is as follows.

In order to inject the IV fluid contained in the IV bag 200 into a patient's blood vessel, the IV tube 220 is connected with the drip chamber 210, the Y-port 250, and the three-way stopcock 260, between the IV bag 200 and the injection site 230.

The IV fluid contained in the IV bag 200 is injected into the patient's blood vessel while flowing to the injection site 230 through the IV tube 220.

Here, when the IV tube 220 through which the IV fluid flows is connected to the IV infusion set, that is, to the drip chamber 210, the injection site 230, the Y-port 250, and the three-way stopcock 260, the connectors 300 that are put on the outer circumferential surface of the IV tube 220 are pushed toward the assembly portion of the IV tube 220 to firmly lock the IV tube 220.

As described above, since the IV tube 220 is locked by the annular ring-shaped connector 300, unlike the conventional method of bonding the IV tube using an adhesive, the adhesive is not injected into the patient along with the IV fluid, whereby it may be safely used.

Further, in the state where the connectors 300 are put on the IV tube 220, the connectors are simply pushed to firmly lock the IV tube 220, whereby it is possible to facilitate manufacturing the IV infusion set.

Further, the insertion part 310 of the connector 300, which is fitted over the IV tube 220, is formed with the tapered portion 311, and the inner wall of the insertion part 310 is provided with the compression piece 320, whereby the connector 300 is smoothly fitted over the IV tube 220 and maximally presses the IV tube 220, such that the IV tube 220 is firmly locked, so it is possible to improve the quality of the IV infusion set.

It is understood by those skilled in the art that the foregoing description is a preferred embodiment of the disclosed device and that various changes and modifications may be made in the invention without departing from the spirit and scope thereof.

DESCRIPTION OF REFERENCE CHARACTERS OF IMPORTANT PARTS

200: IV bag
201: outlet
210: drip chamber
220: IV tube
221: anti-separation groove
230: injection site
231: needle
240: flow control clamp
250: Y-port
260: three-way stopcock
300: connector
310: insertion part
311: tapered portion
320: compression piece

The invention claimed is:

1. A connection structure for an IV tube of an IV infusion set, in which an outlet provided on an IV bag is connected to a drip chamber, the IV tube is connected to the drip chamber to allow an IV fluid to flow, an injection site for injecting the IV fluid into a patient is connected to an end of the IV tube, and a Y-port, a three-way stopcock, a filter, a luer lock, in addition to the drip chamber and the injection site are connected to the IV tube, the connection structure comprising:
    a connector provided on an outer circumferential surface of the IV tube to lock the IV tube, with at least one of the drip chamber, the injection site, the Y-port, the three-way stopcock, the filter, and the luer lock being connected to the IV tube,
    wherein the connector is formed in an annular ring shape to be fitted over the outer circumferential surface of the IV tube, with an insertion part being provided in the connector to allow the IV tube to be inserted therein, and wherein an inner wall of the connector is tapered downward from a top end of the connector such that the IV tube firmly and directly contacts at least one of the drip chamber, the injection site, the Y-port, the three-way stopcock, the filter, and the luer lock at a bottom end of the connector.

2. The connection structure of claim 1, wherein the IV tube is connected with the drip chamber, the injection site, the Y-port, the three-way stopcock, the filter, and the luer lock, wherein the IV tube is connected with each of the drip chamber, the injection site, the Y-port, the three-way stopcock, the filter, and the luer lock, by using the connector.

3. The connection structure of claim 1, wherein the inner wall of the connector is tapered downward.

4. The connection structure of claim 1, wherein the connector completely covers overlapping surfaces of the IV tube and at least one of the drip chamber, the injection site, the Y-port, the three-way stopcock, the filter, and the luer lock that are in direct contact with one another.

5. The connection structure of claim 1, wherein the IV tube and at least one of the drip chamber, the injection site, the Y-port, the three-way stopcock, the filter, and the luer lock respectively enter the bottom end and the top end of the connector.

6. The connection structure of claim 1, wherein the IV tube is between the connector and at least one of the drip chamber, the injection site, the Y-port, the three-way stopcock, the filter, and the luer lock.

7. The connection structure of claim 1, the connection structure further comprising a compression piece, wherein the compression piece is provided on the inner wall of the connector to press the IV tube against at least one of the drip chamber, the injection site, the Y-port, the three-way stopcock, the filter, and the luer lock, such that the IV tube is prevented from being separated therefrom.

8. The connection structure of claim 7, wherein the compression piece is provided in a band shape or a dot shape.

9. The connection structure of claim 7, wherein the outer circumferential surface of the IV tube comprises an anti-separation groove, and wherein the compression piece is engaged with the anti-separation groove when the IV tube is connected to at least one of the drip chamber, the injection site, the Y-port, the three-way stopcock, the filter, and the luer lock to prevent the IV tube from being separated.

10. The connection structure of claim 7, wherein the compression piece protrudes outwardly from the inner wall of the connector.

11. The connection structure of claim 1, wherein the IV tube directly contacts the connector and at least one of the drip chamber, the injection site, the Y-port, the three-way stopcock, the filter, and the luer lock in such a way that an empty space is formed between the top end of the connector and an end of the IV tube in a radial direction, which is perpendicular to a circumferential direction.

12. The connection structure of claim 1, wherein the IV tube directly contacts the drip chamber and the connector.

* * * * *